United States Patent
Morariu

(10) Patent No.: US 9,555,126 B2
(45) Date of Patent: Jan. 31, 2017

(54) USE OF ANTI-CD19 MAYTANSINOID IMMUNOCONJUGATE ANTIBODY FOR THE TREATMENT OF B-CELL MALIGNANCIES SYMPTOMS

(75) Inventor: Rodica Morariu, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/117,806

(22) PCT Filed: May 16, 2012

(86) PCT No.: PCT/EP2012/059141
§ 371 (c)(1),
(2), (4) Date: Nov. 14, 2013

(87) PCT Pub. No.: WO2012/156455
PCT Pub. Date: Nov. 22, 2012

(65) Prior Publication Data
US 2014/0072587 A1    Mar. 13, 2014

(30) Foreign Application Priority Data

May 17, 2011   (EP) .................................... 11290232

(51) Int. Cl.
| | | |
|---|---|---|
| *A61K 39/44* | (2006.01) | |
| *A61K 39/395* | (2006.01) | |
| *A61K 47/48* | (2006.01) | |
| *C07K 16/28* | (2006.01) | |
| *A61K 45/06* | (2006.01) | |
| *A61K 39/00* | (2006.01) | |

(52) U.S. Cl.
CPC ........... *A61K 47/4863* (2013.01); *A61K 45/06* (2013.01); *A61K 47/48384* (2013.01); *A61K 47/48561* (2013.01); *C07K 16/2803* (2013.01); *A61K 2039/505* (2013.01); *C07K 2317/24* (2013.01); *C07K 2317/77* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 2003/0105000 A1* | 6/2003 | Pero | ....................... | A61K 38/06 514/19.3 |
| 2008/0138336 A1* | 6/2008 | Damschroder | .... | C07K 16/2803 424/133.1 |
| 2014/0199300 A1* | 7/2014 | Besret | .............. | A61K 39/39558 424/133.1 |

FOREIGN PATENT DOCUMENTS

| | | |
|---|---|---|
| EP | 1651162 | 12/2004 |
| WO | 2004103272 A2 | 12/2004 |
| WO | 2010128087 A2 | 11/2010 |
| WO | 2011050180 A1 | 4/2011 |

OTHER PUBLICATIONS

Tannock, I.F. (Experimental Chemotherapy, Ch. 19-p. 338 and 352-359, in The Basic Science of Oncology Tannock and Hill, eds., New York 1992).*

(Continued)

*Primary Examiner* — Peter J Reddig
(74) *Attorney, Agent, or Firm* — McCarter & English, LLP; Steven G. Davis; Xin Zhang

(57) ABSTRACT

An anti-CD19 maytansinoid immunoconjugate is used for treating B-cell malignancies symptom, in particular Non-Hodgkin's lymphoma.

22 Claims, 4 Drawing Sheets

(56) References Cited

OTHER PUBLICATIONS

Figure 1:
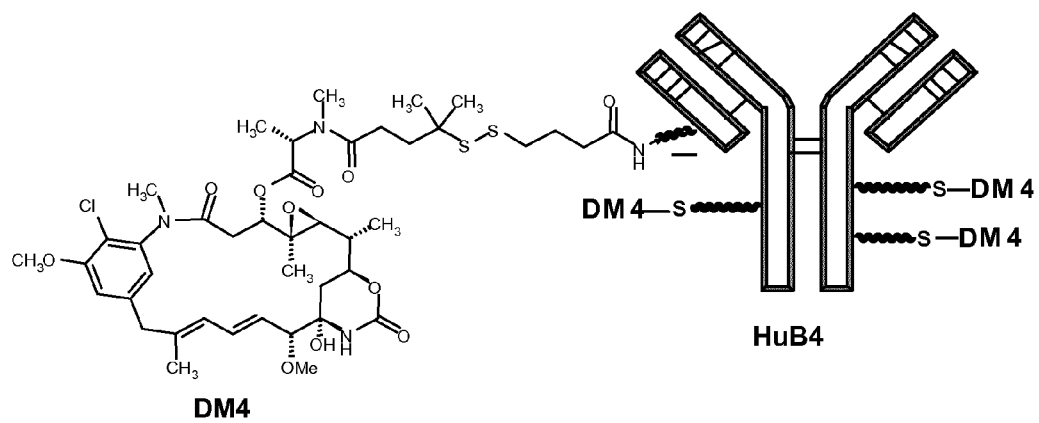

Rudikoff et al. (PNAS USA, 1982, 79: 1979-1983).*
Coleman et al. (Research in Immunology, 1994; 145(1): 33-36).*
Burgess et al. (J. of Cell Biol. 111:2129-2138, 1990).*
Ibragimova and Wade (Biophysical Journal, Oct. 1999, vol. 77, pp. 2191-2198).*
Common Terminology Criteria for Adverse Events (CTCAE) Published May 28, 2009 by the U.S.Department of Health and Human Services.
Helft et al., "A Phase I Study of Cantuzumab Mertansine Administered as a single Intravenous infusion Once Weekly in Patients with Advanced Solid Tumors," Clinical Cancer Research, vol. 10, pp. 4363-4368, 2004.
International Search Report for PCT/EP2012/059141 as mailed on Aug. 3, 2012.
Lock et al., "192 Poster: Pediatric Preclinical Testing Program (PPTP) evaluation of the anti-CD19-DM4 conjugated antibody SAR3419," Eur. J. Cancer Suppl., vol. 6 No. 12 p. 61 (2008).
National Cancer Institute Common Terminology Criteria for Adverse Events version3, Aug. 9, 2006.
Roguska et al. "Humanization of murine monoclonal antibodies through variable domain resurfacing," Proc. Natl. Acad. Sci. USA, 91: 969-973, 1994.
Younes et al, "Phase I Multi-Dose Escalation Study of the Anti-CD19 Maytansinoid Immunoconjugate SAR3419 Administered by intravenous (IV) Infusion Every 3 Weeks to Patients with Relapsed Refractory B-Cell Non-Hodgkin's Lymphoma (NHL)," Ash Annual Meeting Abstracts, 2009, 114(22):585.
Al-Katib et al., "Superior Antitumor Activity of SAR3419 to Rituximab in Xenograft Models for Non-Hodgkin's Lymphoma," Clin. Cancer Res. 15(12): 4038-4045 (2009).
ClinicalTrials Identifier: NCT00796731, Clinicaltrials.gov archive (updated Apr. 13, 2011, search on Jan. 2, 2016) 4 pages.
Roguska, et al., "A comparison of two murine monoclonal antibodies humanized by CDR-grafting and variable domain resurfacing." Protein Eng. 9(10): 895-904 (1996).
Smith, "Update on developmental therapeutics for acute lymphoblastic leukemia," Curr Hematol Malig Rep. 4(3): 175-182 (2009).
Younes et al., "Phase 1 multidose-escalation study of the anti-CD19 maytansinoid immunoconjugate SAR3419 administered by intravenous infusion every 3 weeks to patients with relapsed/refractory B-cell lymphoma." J Clin Oncol. 30(22):2776-82 (2012).

* cited by examiner

```
                            SEQUENCE LISTING

<160> NUMBER OF SEQ ID NOS: 8

<210> SEQ ID NO 1
<211> LENGTH: 10
<212> TYPE: PRT
<213> ORGANISM: Mus musculus
<220> FEATURE:
<221> NAME/KEY: misc_feature
<223> OTHER INFORMATION: CDR L1

<400> SEQUENCE: 1

Ser Ala Ser Ser Gly Val Asn Tyr Met His
1               5                   10

<210> SEQ ID NO 2
<211> LENGTH: 7
<212> TYPE: PRT
<213> ORGANISM: Mus musculus
<220> FEATURE:
<221> NAME/KEY: misc_feature
<223> OTHER INFORMATION: CDR L2 sequence

<400> SEQUENCE: 2

Asp Thr Ser Lys Leu Ala Ser
1               5

<210> SEQ ID NO 3
<211> LENGTH: 7
<212> TYPE: PRT
<213> ORGANISM: Mus musculus
<220> FEATURE:
<221> NAME/KEY: misc_feature
<223> OTHER INFORMATION: CDR L3 sequence

<400> SEQUENCE: 3

His Gln Arg Gly Ser Tyr Thr
1               5

<210> SEQ ID NO 4
<211> LENGTH: 5
<212> TYPE: PRT
<213> ORGANISM: Mus musculus
<220> FEATURE:
<221> NAME/KEY: misc_feature
<223> OTHER INFORMATION: CDR H1 sequence

<400> SEQUENCE: 4

Ser Asn Trp Met His
1               5

<210> SEQ ID NO 5
<211> LENGTH: 10
<212> TYPE: PRT
<213> ORGANISM: Mus musculus
<220> FEATURE:
<221> NAME/KEY: misc_feature
<223> OTHER INFORMATION: CDR H2 sequence

<400> SEQUENCE: 5

Glu Ile Asp Pro Ser Asp Ser Tyr Thr Asn
1               5                   10
```

```
<210> SEQ ID NO 6
<211> LENGTH: 11
<212> TYPE: PRT
<213> ORGANISM: Mus musculus
<220> FEATURE:
<221> NAME/KEY: misc_feature
<223> OTHER INFORMATION: CDR H3 sequence

<400> SEQUENCE: 6

Gly Ser Asn Pro Tyr Tyr Tyr Ala Met Asp Tyr
1               5                   10

<210> SEQ ID NO 7
<211> LENGTH: 211
<212> TYPE: PRT
<213> ORGANISM: Artificial
<220> FEATURE:
<223> OTHER INFORMATION: huB4 Light Chain Sequence

<400> SEQUENCE: 7

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 8
<211> LENGTH: 450
<212> TYPE: PRT
<213> ORGANISM: Artificial
<220> FEATURE:
<223> OTHER INFORMATION: huB4 Heavy Chain Sequence

<400> SEQUENCE: 8

Gln Val Gln Leu Val Gln Pro Gly Ala Glu Val Val Lys Pro Gly Ala
1               5                   10                  15
```

```
Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
            35                  40                  45

Gly Glu Ile Asp Pro Ser Asp Ser Tyr Thr Asn Tyr Asn Gln Asn Phe
 50                  55                  60

Gln Gly Lys Ala Lys Leu Thr Val Asp Lys Ser Thr Ser Thr Ala Tyr
 65                  70                  75                  80

Met Glu Val Ser Ser Leu Arg Ser Asp Thr Ala Val Tyr Tyr Cys
                 85                  90                  95

Ala Arg Gly Ser Asn Pro Tyr Tyr Tyr Ala Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

USE OF ANTI-CD19 MAYTANSINOID IMMUNOCONJUGATE ANTIBODY FOR THE TREATMENT OF B-CELL MALIGNANCIES SYMPTOMS

The present invention relates to the use of anti-CD19 maytansinoid immunoconjugate for the treatment of B-cell malignancies symptom.

Cell surface molecules expressed by B cells and their malignant counterparts represent important targets for immunotherapy.

CD19 is the earliest differentiation antigen of the B lymphocyte lineage, expressed on most B cells, but not detected on plasma cells, stem cells, or on normal myeloid lineage.

Therefore, CD19 is expressed on tumor cells from all B cell derived neoplasms (Bcell non-Hodgkin's lymphoma, acute lymphoblastic leukemia, chronic lymphocytic leukemia) except myeloma.

B-cell Non-Hodgkin's lymphoma (B-NHL) is the fifth most common malignancy in the United States and continues to increase in incidence, especially in elderly patients. While patients with hematological malignancies have benefited over the past decade from therapeutic optimization using conventional drug therapy, a majority of patients still succumb to their disease and drug therapies remain highly toxic. Hence, future efforts towards developing new therapies to improve survival and quality of life of lymphoma patients must include strategies that specifically targets cancer cells and show improved safety and efficacy.

HuB4-DM4 is an antibody-drug conjugate composed of a humanized IgG1 monoclonal antibody, huB4, which specifically targets the CD19 antigen, conjugated through a disulfide link to the maytansinoid derivative DM4, a potent tubulin inhibitor. The structure of the HuB4-DM4 conjugate SAR3419 is disclosed on FIG. 1 and the sequence of the heavy and light chains of the antibody are listed in the enclosed sequence listing, said light chain having the sequence represented in SEQ ID NO. 7, and said heavy chain having the sequence represented in SEQ ID NO. 8.

After binding to the CD19 antigen, the HuB4-DM4 conjugate undergoes internalization and intracellular release of DM4.

In the first-in-man study TED6828 the HuB4-DM4 conjugate SAR3419 administered IV once every 3 weeks for 6 cycles (N=39) in patients with refractory/relapsed CD19+ NHL, 7 dose levels (10 mg/m$^2$ to 270 mg/m$^2$) was tested. The Maximum Tolerated Dose (MTD) was 160 mg/m$^2$ every 3 weeks. The dose limiting toxicity was reversible corneal toxicity. The most frequent drug related toxicity was ocular (all grades) observed in 43.5% of patients, 15.4% being of grade ¾. The toxicities consisting mainly of blurred vision associated with microcystic deposits on the corneal epithelium (corneal toxicities) were reversible in all cases.

The preliminary results of this trial have been published in the abstracts of the ASH 2009 (Younes et al, ASH ANNUAL Meeting Abstracts, 2009, 114(22):585).

It has now been found that it is possible to reduce the toxicity, and in particular the ocular toxicity, resulting from the treatment with the HuB4-DM4 conjugate by administering the HuB4-DM4 conjugate with another dosage regimen.

It has furthermore been shown that the conjugate SAR3419 allows treating patients having B-cell Non-Hodgkin's lymphoma, in particular Diffuse Large B-cell lymphoma (DLBCL).

The invention relates to methods, compositions and articles as disclosed herein.

In one aspect the invention provides for a method of treating CD19+ B-cell malignancies symptom in a patient in need thereof, said method comprising administering to said patient therapeutically effective amounts of anti-CD19 maytansinoid immunoconjugate.

In a particular embodiment said method comprises administering to said patient therapeutically effective amounts of anti-CD19 maytansinoid immunoconjugate with a dose regimen reducing the ocular toxicity resulting from the treatment.

In an embodiment this toxicity results from the treatment with the HuB4-DM4 conjugate.

In another particular embodiment of this method the occurrence of eye related adverse events (all grades) is below 40%.

In another particular embodiment of this method the occurrence of eye related adverse events grade 3 or 4 is below 13%.

This method is safe and effective.

Although the present invention relates primarily to the treatment of CD19+ B-cell malignancies symptom in a patient in need thereof, B-cell malignancies symptom whatever the level of expression of CD19 in the cells can be also treated.

Thus in another aspect the invention provides for a method of treating B-cell malignancies symptom in a patient in need thereof, said method comprising administering to said patient therapeutically effective amounts of anti-CD19 maytansinoid immunoconjugate.

These methods of treating can comprise the steps of administering to the patient an initial dose of about 55 mg/m$^2$ of the anti-CD19 maytansinoid immunoconjugate and administering to the patient a plurality of subsequent doses of about 55 mg/m$^2$ of the anti-CD19 maytansinoid immunoconjugate, wherein the subsequent doses are separated in time from each other by about one week.

In a particular embodiment of this method the administration of the initial dose is followed by the administration of at least 6 doses separated in time from each other by one week. In another embodiment the initial dose is followed by the administration of at least 7 or 8 doses separated in time from each other by about one week.

In another particular embodiment of this method the administration of the initial dose is followed by the administration of between 6 and 14 doses separated in time from each other by about one week. In another embodiment the administration of the initial dose is followed by the administration of between 7 and 13 doses or 8 to 12 doses.

Thus in this particular embodiment said method comprises the steps of:
  administering to the patient an initial dose of about 55 mg/m$^2$, of the anti-CD19 maytansinoid immunoconjugate, and
  administering to the patient at least 6 subsequent doses of about 55 mg/m$^2$ separated in time from each other by about one week of the anti-CD19 maytansinoid immunoconjugate.

This method of treating can comprise a further step of administration of subsequent doses of about 55 mg/m$^2$ of anti-CD19 maytansinoid immunoconjugate wherein the doses are separated in time from each other by about two weeks.

In this particular embodiment of this method the administration of the initial dose is followed by the administration of at least 3 doses separated in time from each other by about one week and then by the administration of at least 3 doses separated in time from each other by about two weeks. This embodiment is generally referred to weekly/2 weekly or qw/q2w or even optimized schedule in the present application.

Thus in this particular embodiment said method comprises the steps of:
- administering to the patient an initial dose of about 55 mg/m², of the anti-CD19 maytansinoid immunoconjugate,
- administering to the patient at least 3 subsequent doses of about 55 mg/m² separated in time from each other by about one week of the anti-CD19 maytansinoid immunoconjugate, and
- administering to the patient at least 3 subsequent doses of about 55 mg/m² of the anti-CD19 maytansinoid immunoconjugate separated in time from each other by about two weeks.

CD19+ B-cell malignancies are defined as any malignancies expressing the CD19 cell surface antigen.

Said CD19+ B-cell malignancies symptom can be a leukemia symptom, such as Acute lymphoblastic leukemia (ALL) symptom or a lymphoma symptom, such as a Non-Hodgkin's lymphoma symptom (NHL) symptom.

The Non-Hodgkin's lymphoma symptom can be a Diffuse Large B-cell lymphoma (DLBCL), a folicullar lymphoma (FL), a Mantle cell lymphoma (MCL), a Marginal zone lymphoma (MZL), a Small lymphocytic lymphoma (SLL) or a Waldenström macroglobulinemia (WM).

In a particular embodiment of this method said Non-Hodgkin's lymphoma symptom is a relapsed or refractory B-cell non-Hodgkin's lymphoma.

In another particular embodiment of this method the said Non-Hodgkin's lymphoma symptom is a B-cell non-Hodgkin's lymphoma expressing CD19.

In another particular embodiment of this method the said patient has already been treated for the Non-Hodgkin's lymphoma symptom. In particular said patient may have failed therapy, and in particular a chemotherapy or a rituximab therapy.

In another particular embodiment of this method the said Non-Hodgkin's lymphoma symptom is a rituximab resistant disease.

In another particular embodiment of this method the said patient has received a autologous or allogeneic stem cell transplant.

In a particular embodiment of this method the anti-CD19 maytansinoid immunoconjugate comprises an antibody which binds specifically to the CD19 antigen conjugated to DM4.

The antibody which binds specifically to the CD19 antigen can be conjugated to DM4 through a cleavable linker, in particular a N-succinimidyl 4-(2-pyridyldithio)butanoate (SPDB) linker.

In a particular embodiment of this method the anti-CD19 maytansinoid immunoconjugate comprises an antibody which binds specifically to the CD19 antigen conjugated to DM4 through SPDB wherein about 3.5 molecules of DM4 are bound through the SPDB linker to each huB4 molecule.

In a particular embodiment the anti-CD19 maytansinoid immunoconjugate has the following formula:

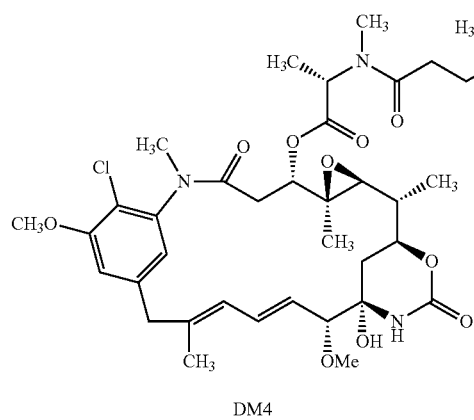

DM4

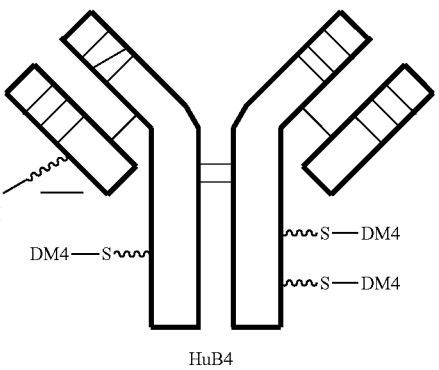

HuB4

In an embodiment, the said antibody comprises six complementary determining region (CDR), said CDR having the sequences represented in SEQ ID NOs 1 to 6.

In another embodiment, the antibody comprises a light chain, wherein the sequence of the said light chain has at least 60%, at least 75%, at least 85%, at least 95% or at least 99% identity with the sequence displayed in SEQ ID NO. 7.

In yet another embodiment, the antibody comprises a heavy chain, wherein the sequence of the said heavy chain has at least 60%, at least 75%, at least 85%, at least 95% or at least 99% identity with the sequence displayed in SEQ ID NO. 8.

In another embodiment, the antibody of the invention is the humanized antibody huB4 described in Roguska et al. (*Proc. Natl. Acad. Sci. USA,* 91: 969-973, 1994). The antibody huB4 according to the invention comprises a light chain and a heavy chain, said light chain having the sequence represented in SEQ ID NO. 7, and said heavy chain having the sequence represented in SEQ ID NO. 8. in a particular embodiment the conjugate is the HuB4-DM4 conjugate.

In one aspect the invention provides for anti-CD19 maytansinoid immunoconjugate for treating a human patient diagnosed with a CD19+ B-cell malignancies symptom with a method comprising the steps of administering to the patient an initial dose of about 55 mg/m² of the anti-CD19 maytansinoid immunoconjugate; and administering to the patient a plurality of subsequent doses of about 55 mg/m², of the anti-CD19 maytansinoid immunoconjugate, wherein the subsequent doses are separated in time from each other by one week.

In one aspect the invention provides for anti-CD19 maytansinoid immunoconjugate for treating a human patient diagnosed with a CD19+ B-cell malignancies symptom with a method comprising the steps of administering to the patient an initial dose of about 55 mg/m² of the anti-CD19 maytansinoid immunoconjugate; and then administering to the patient a plurality of subsequent doses of about 55 mg/m², of the anti-CD19 maytansinoid immunoconjugate separated in time from each other by one week, and in a further step administering a plurality of subsequent doses of about 55 mg/m² of the anti-CD19 maytansinoid immunoconjugate separated in time from each other by two weeks.

In another aspect the invention provides for an article of manufacture comprising:
a packaging material
an anti-CD19 maytansinoid immunoconjugate, and
a label or package insert contained within said packaging material indicating that said anti-CD19 maytansinoid immunoconjugate is administered to the patient at an initial dose of about 55 mg/m², and in a plurality of subsequent doses separated in time from each other by one week in an amount that is about 55 mg/m².

In another aspect the invention provides for an article of manufacture comprising:
a packaging material
an anti-CD19 maytansinoid immunoconjugate, and
a label or package insert contained within said packaging material indicating that said anti-CD19 maytansinoid immunoconjugate is administered to the patient at an initial dose of about 55 mg/m², then in a plurality of subsequent doses separated in time from each other by one week in an amount that is about 55 mg/m² and then in a plurality of subsequent doses separated in time from each other by two weeks in an amount that is about 55 mg/m².

In one aspect the invention provides for article of manufacture comprising:
a packaging material
an anti-CD19 maytansinoid immunoconjugate, and
a label or package insert contained within said packaging material indicating that said anti-CD19 maytansinoid immunoconjugate is administered to the patient at a dose of about 55 mg/m² to minimize the risks of toxicity, such as the late and cumulated toxicities and in particular the risks of ocular toxicity.
Such a packaging material indicating that said anti-CD19 maytansinoid immunoconjugate is administered to the patient at a dose of about 55 mg/m² (4 doses separated in time from each other by one week and then 4 subsequent doses separated in time from each other by two weeks) with to limit the accumulation of the drug thought to be the cause—at least in part—of cumulative toxicities or of the increase severity of such toxicities, such as corneal toxicities, peripheral sensory neuropathy and paresthesias.

In a particular embodiment the label or package insert contained within said packaging material indicates that the occurrence of eye related adverse events (all grades) is below 40%, 30% or 25%.

In a particular embodiment the label or package insert contained within said packaging material indicates that the occurrence of eye related adverse events grade ¾ is below 13%, 10% or 5')/0.

The ocular toxicity is characterized by the eye disorders observed in the patients.

The eye disorders are defined in the Version 3.0 of the document entitled "Common Terminology Criteria for Adverse Events (CTCAE)" Published in May 28, 2009 by the U.S. DEPARTMENT OF HEALTH AND HUMAN SERVICES to which the man skilled in the art may refer.

According to this document the eye disorders are classified by adverse events (AE) that are graded depending on their severity.

The CTCAE displays Grades 1 through 5 with unique clinical descriptions of severity for each AE based on this general guideline:
Grade 1 Mild; asymptomatic or mild symptoms; clinical or diagnostic observations only; intervention not indicated.
Grade 2 Moderate; minimal, local or non-invasive intervention indicated; limiting age-appropriate instrumental activities of daily living (ADL).
Grade 3 Severe or medically significant but not immediately life-threatening; hospitalization or prolongation of hospitalization indicated; disabling; limiting self care ADL.
Grade 4 Life-threatening consequences; urgent intervention indicated.
Grade 5 Death related to AE.

The anti-CD19 maytansinoid immunoconjugate can be administered within a pharmaceutical compositions comprising:
an effective amount of anti-CD19 maytansinoid immunoconjugate, and
a pharmaceutically acceptable carrier, which may be inert or physiologically active.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20.

In another embodiment, the anti-CD19 maytansinoid immunoconjugate is administered intravenously. However other mode of parenteral administration can be used: e.g. intramuscular, intraperinoneal or subcutaneous.

When the anti-CD19 maytansinoid immunoconjugate is administered intravenously it can be administered as a bolus or by continuous infusion over a period of time that is typically comprised between 10 minutes and 4 hours.

In another embodiment, they are injected by intramuscular, subcutaneous, intra-articular, intrasynovial, intratumoral, peritumoral, intralesional, or perilesional routes, to exert local as well as systemic therapeutic effects. They can be also administered by nebulisation.

The anti-CD19 maytansinoid immunoconjugate may be administered in a variety of forms. These include for example liquid, semi-solid, and solid dosage forms, but the form depends on the intended mode of administration and therapeutic application.

Typical compositions are in the form of injectable or infusible solutions.

Sterile compositions for parenteral administration can be prepared by incorporating the anti-CD19 maytansinoid immunoconjugate in the required amount in the appropriate solvent, followed by sterilization by microfiltration. As solvent or vehicle, there may be used water, saline, phosphate buffered saline, dextrose, glycerol, ethanol, and the like, as well as a combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The anti-CD19 maytansinoid immunoconjugate may be administered with a further therapeutic agent, such a chemotherapeutic agent, as necessary for the particular disorder being treated. Preferably, the anti-CD19 maytansinoid immunoconjugate and the supplementary active agent will have complementary activities that do not adversely affect each other.

Such a chemotherapeutic agent may be administered simultaneously, semi-simultaneously, separately, or spaced out over a period of time so as to obtain the maximum efficacy of the co-administration; it being possible for each administration to vary in its duration from a rapid administration to a continuous perfusion.

The man skilled in the art may refer in particular to EP1651162 to carry out the present invention.

FIGURES

Figure 2:
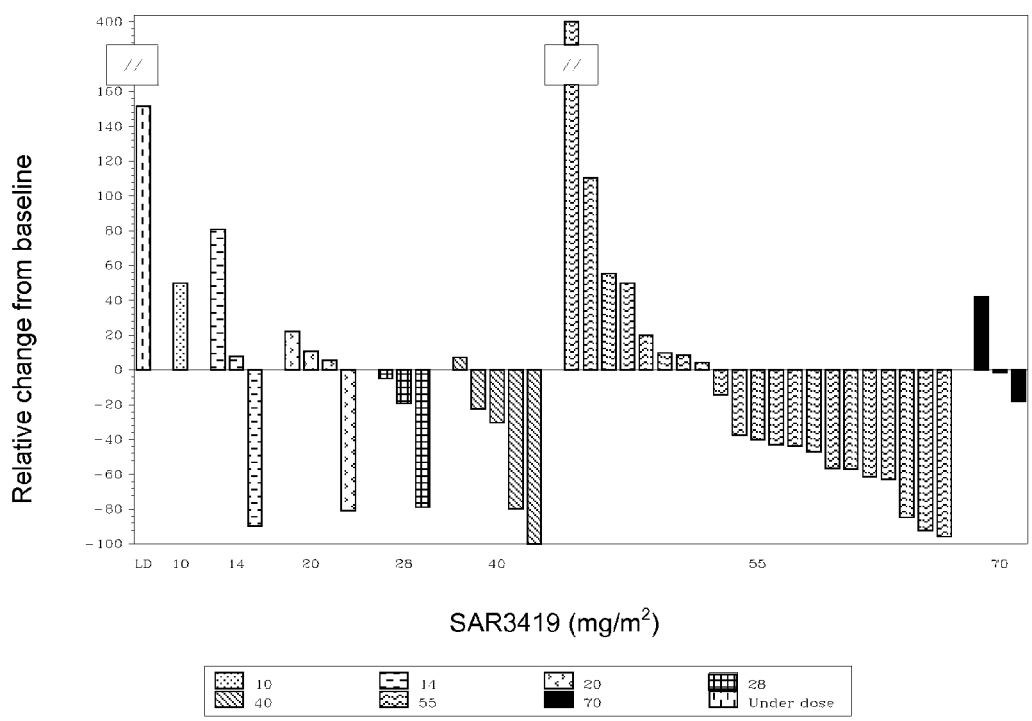
Figure 3:
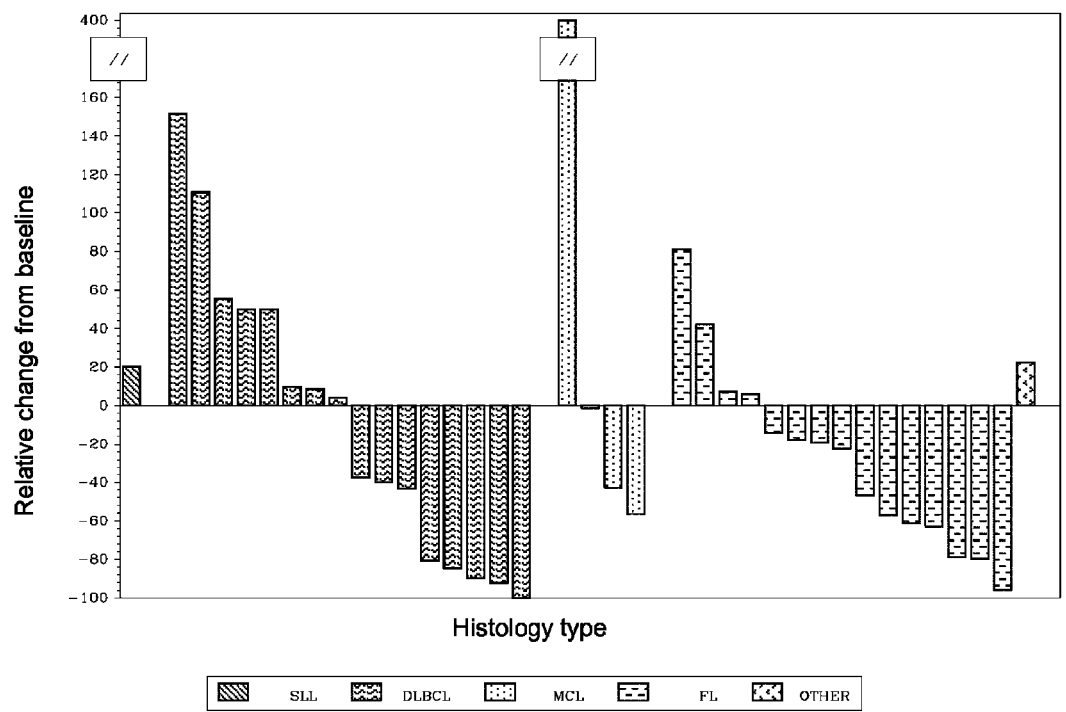
Figure 4:
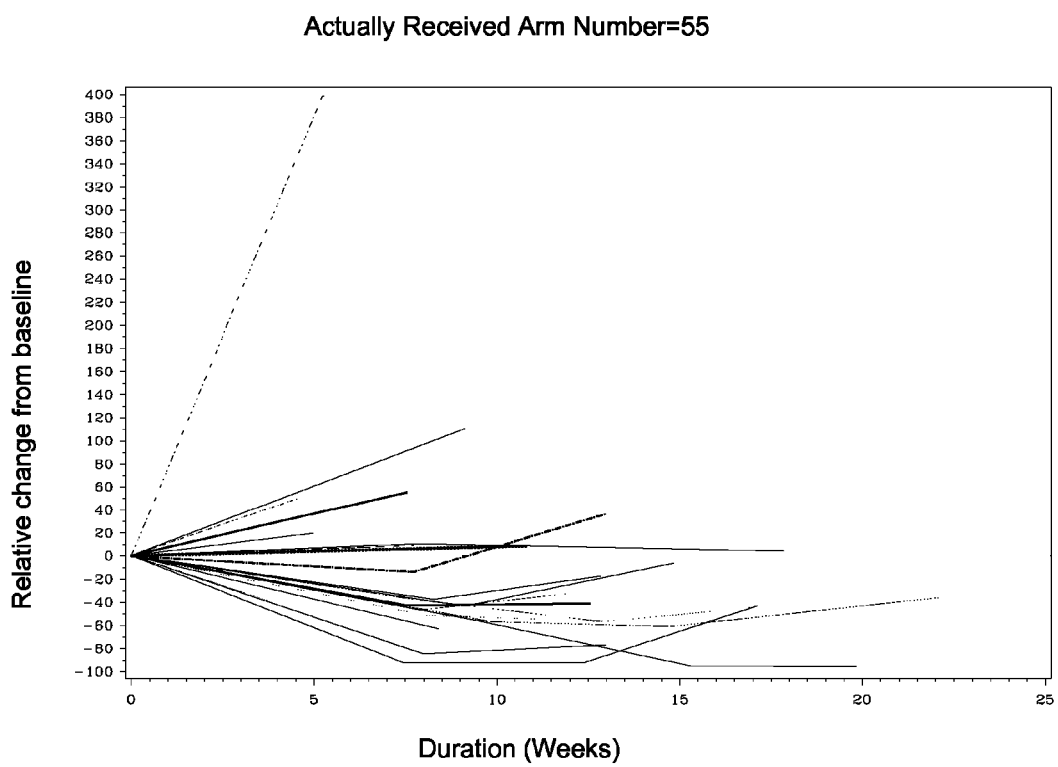

FIG. 1: structure of the HuB4-DM4 conjugate SAR3419.
FIG. 2: treatment response by dose level.
FIG. 3: treatment response by histology.
FIG. 4: tumor shrinkage over time at the MTD.

The following example illustrates a combination according to the invention.

EXAMPLE 1

HuB4-DM4 Conjugate Administered Weekly in Patients with Relapsed/Refractory CD19-positive B-cell Non-Hodgkin's Lymphoma (Study TED6829)

Study Objectives
Primary:
  To determine the maximal tolerated dose (MTD) of SAR3419 according to the Dose Limiting Toxicities (DLTs) observed when administered IV, as a single agent, once weekly in patients with relapsed or refractory B-cell NHL.
Secondary:
  To characterize the global safety profile of SAR3419
  To evaluate the pharmacokinetic (PK) profile of SAR3419
  To perform pharmacodynamic (PD) assessments
  To assess the potential immunogenicity of SAR3419
  To assess preliminary evidence of anti-lymphoma activity Methods
Study Design
  Adult patients with refractory or relapsed B-cell NHL expressing the CD19 antigen were enrolled.
  Dose escalation was based on safety in a 3+3 design.
  The dose-escalation was guided by the occurrence of pre-defined DLT during the initial 3 week period of treatment. Late or cumulative toxicities during the treatment period could also be considered for defining the recommended dose.
  SAR3419 Drug Product was available as a solution for infusion at 25 mg/25 mL (1 mg/mL) with reference to the active entity supplied in a 30 mL clear glass vial.
  SAR3419 as single agent was administered IV once weekly for 8 doses. Any further treatment that may be of clinical benefit for the patient could be discussed and agreed between the investigators and the sponsor.
  Premedication with diphenhydramine 50 mg IV and acetaminophen 650 mg per os was required prior to each infusion.
Evaluations
  Computed Tomography (CT) and/or Positron Emission Tomography (PET) scan performed at study entry, after 8 doses and 42-49 days after the last treatment (EOT). Responders were followed every 3 months for up to 1 year.
  PK and immunogenicity assessments were performed using blood samples collected at baseline, at specific time-points during the treatment and at EOT.
Results
  The results are summarized in the following tables 1-7.

TABLE 1

Baseline Demographics and Disease Characteristic

|  | N | |
| --- | --- | --- |
| Treated | 44 | |
| Dose escalation/dose expansion | 28/16 | |
| Evaluable for safety | 44 | |
| Evaluable for response | 43 | |
| Age, median (range) | 67 (36-82) | |
| Male/Female | 30/14 | |

| Histology | Initial diagnosis | Study entry* |
| --- | --- | --- |
| FL | 19 (43%) | 15 (34%) |
| DLBCL | 16 (36%) | 17 (39%) |
| MCL, MZL, SLL, mixed | 3, 4, 1, 1 | 4, 0, 1, 1 |

| | | |
| --- | --- | --- |
| Stage III/IV at study entry | 39 (89%) | |
| Median number of prior regimens | 3 (1-8) | |
| Patients with prior rituximab therapy | 43 (98%) | |
| Patients with rituximab resistant disease | 21 (48%) | |
| Prior stem cell transplant autologous/allogeneic | 18 (41%)/1 (2%) | |

*6 missing histologies at study entry.

TABLE 2

Dose escalation

| Dose level (mg/m²/week) | Patients enrolled (intented dose) | Patients enrolled (actual dose)*** | Patient with predefined DLT Predefined DLT period | Treatment period |
| --- | --- | --- | --- | --- |
| <10 | | 1 | 0 | 0 |
| 10 | 3 | 3 | 0 | 0 |

TABLE 2-continued

Dose escalation

| Dose level (mg/m²/week) | Patients enrolled (intented dose) | Patients enrolled (actual dose)*** | Patient with predefined DLT Predefined DLT period | Treatment period |
|---|---|---|---|---|
| 14 | 3 | 3 | 0 | 0 |
| 20 | 4 | 4 | 0 | 0 |
| 28 | 3 | 3 | 0 | 0 |
| 40 | 3 | 5 | 0 | 0 |
| 55** | 22 | 21 | 0 | 0 |
| 70 | 6 | 4 | 1* | 1* |

*1 patient had a DLT after 2 doses: grade 3 neutropenia leading to a 2 week-dose delay. 2 patients treated at 70 mg/m2 had late (>5 doses) grade 2 significant toxicities: blurred vision associated with corneal deposits and left bundle branch block which were taken into account for dose escalation.
**The study defined 55 mg/m2 as the MTD/RD (Recommended Dose).
*** One investigative site mistakenly did not flush the IV line at each study drug infusion. A 18 ml-dead volume of the preparation corresponding to 18 mg of study drug was not administered. Eight patients that were enrolled at this site were retrospectively reassigned to their actual dose level. Study results are provided based on the actual dose level.

TABLE 3

Non heamotological Related TEAE grade 3-4

| Adverse Events* | Dose Levels (mg/m²/week) | | | | | | | |
|---|---|---|---|---|---|---|---|---|
| | <10 (n = 1) | 10 (n = 3) | 14 (n = 3) | 20 (n = 4) | 28 (n = 3) | 40 (n = 5) | 55*** (n = 21) | 70 (n = 4) |
| Increased gamma-glutamyltransferase | | | | | | | 1 | |
| Cholestasis | 1 | | | | | | 1 | |
| Optic neuropathy | | | | | | | 1** | |
| Paresthesia | | | | | | | 2 | |
| Lobar pneumonia | | | | | | | 1** | |
| Alveolitis allergic | | | | | | | 1** | |
| Progressive multifocal leukoencephalopathy | | | 1** | | | | | |

*Adverse events were graded according to the National Cancer Institute Common Terminology Criteria for Adverse Events version3.
**A total of 5 related SAE were reported, with 4 being of grade 3-4.
***At the MTD, 2 patients of the expansion cohort had reversible grade 3 toxicities after 6-8 weekly doses: optic neuropathy and paresthesia. These late and cumulative toxicities were considered for amending the study protocol in July 2010 and modifying the administration schedule.

TABLE 4

Hematological toxicity grade 3-4

| Laboratory raw data | Dose Levels (mg/m²/week) | | | | | | | |
|---|---|---|---|---|---|---|---|---|
| | <10 (n = 1) | 10 (n = 3) | 14 (n = 3) | 20 (n = 4) | 28 (n = 3) | 40 (n = 5) | 55 (n = 21) | 70 (n = 4) |
| Neutropenia | 1 | 1 | | 1 | | | 3 | 1 |
| Leukopenia | 1 | | | | | | 3 | 1 |
| Thrombocytopenia | | | | | | | 3 | |
| Anemia | | | | | | | 5 | |

TABLE 5

Related Ocular toxicity

| | Dose Levels (mg/m²/week) | | | | | | | |
|---|---|---|---|---|---|---|---|---|
| | <10 (n = 1) | 10 (n = 3) | 14 (n = 3) | 20 (n = 4) | 28 (n = 3) | 40 (n = 5) | 55 (n = 21) | 70 (n = 4) |
| Eye disorders grade 1-2* | | | | 1 | | 1 | 6 | 1 |
| Eye disorders grade 3** | | | | | | | 1 | |

*include blurred vision (5), dry eye (3), conjunctivitis (1), diplopia (2), eye irritation (1), corneal deposits (1), keratitis (1), keratoconjunctivitis (1), scotoma (1)
**Optic neuropathy (with associated grade 3-4 symptoms blurred vision and eye irritation) is the unique ocular toxicity of grade > 2 reported within the study.

TABLE 6

Anti-lymphoma activity

| | |
|---|---|
| ORR (CR/PR) at «active doses» (>10 mg//m²) | 12/40 (30%) |
| Response rate at MTD | 7/21 (33%) |
| NHL subtypes at study entry | |
| DLBCL | 5/15 |
| FL | 6/15 |
| Response duration (weeks) | [5; 55+]* |

3 patients still responding at the study cut-off date

TABLE 7

Median (CV % or Min-Max) SAR3419 plasma pharmacokinetic parameters observed after repeated administration of SAR3419 (8-12 doses) in the weekly schedule

| Treatment | 10 mg/m² | 14 mg/m² | 20 mg/m² | 28 mg/m² | 40 mg/m² | 55 mg/m² | 70 mg/m² |
|---|---|---|---|---|---|---|---|
| N | 1 | 3 | 3 | 3 | 3 | 16 | 1 |
| Week of Treatment (week) | 8 | 8 (8-8) | 8 (8-8) | 8 (8-8) | 12 (8-12) | 8 (8-12) | 8 |
| Dose (mg/m²) | 4.6 | 14.0 (14.0-16.9) | 19.6 (19.6-20.0) | 28.2 (27.2-30.4) | 45.1 (40.0-45.1) | 55.2 (53.2-61.9) | 70.5 |
| $C_{max}$ (µg/mL) | 2.01 | 11.4 (30) | 14.2 (31) | 22.8 (31) | 35.3 (30) | 47.4 (33) | 94.7 |
| $t_{max}$ (day) | 0.03 | 0.03 (0.02-0.06) | 0.02 (0.02-0.19) | 0.04 (0.03-0.05) | 0.06 (0.04-3.89) | 0.07 (0.06-1.00) | 0.07 |
| $t_{last}$ (day) | 15.01 | 23.0 (22.0-42.0) | 42.8 (14.80-48.11) | 21.0 (6.89-38.9) | 41.9 (6.89-43.95) | 20.0 (2.93-48.0) | 48.0 |
| $AUC_{0-7}$ (day · µg/mL) | 8.07 | 50.7 (31) | 67.3 (44) | 84.6 (65) | 155 (30) | 219 (44) | 298 |
| $T_{1/2}$ (day) | 5.46 | 8.72 (9) | 13.5 (70) | 5.28 (73) | 9.8 (1) | 7.93 (47) | 13.0 |
| CLss (L/day) | 1.12 | 0.58 (34) | 0.817 (0.435-1.20) | 0.79 (75) | 0.60 (0.507-0.32 | 0.32 (49) | 0.442 |
| Vss (L) | 0.14 | 5.94 (1) | 6.12 (5.96-6.29) | 2.20 (95) | 3.32 (0.04-6.55) | 1.91 (66) | 5.03 |

Conclusions

Using weekly schedule of SAR3419 for 8-12 doses, the maximum tolerated dose is 55 mg/m²/week.

SAR3419 demonstrates encouraging activity in both indolent and aggressive NHL with an ORR of 33% at the MTD.

Tumor shrinkage was observed in 25 (58%) patients.

Globally SAR3419 is well tolerated with a median number of doses per patient of 8 overall, and a median relative dose intensity of 0.96 at the MTD. Noteworthy is the lack of significant myelosuppression, making SAR3419 an appealing ADC to be combined with conventional chemotherapy . . . . In the weekly schedule, the ocular toxicity (all grades) is 22% (2% grade ¾) whereas in the 3 weeks administration regimen the ocular toxicity (all grades) was 43.5% with 15.4% of grade ¾.

Paired pre- and post-treatment biopsies allowed to show DM4 accumulation in tumors decrease in CD19 protein expression level and mitosis blockade confirming the mechanism of action of the drug.

Based on the clinical evidence of two grade 3 toxicities (optic neuropathy and paresthesia) with late onset supported by PK data showing drug accumulation after weekly dosing, the protocol was amended to evaluate an optimized schedule consisting of 4 weekly doses of 55 mg/m² followed by 4 additional doses administered once every 2 weeks.

EXAMPLE 2

HuB4-DM4 Conjugate Administered Weekly and then Bi-Weekly (Qw/Q2w Schedule) in Patients with Relapsed/Refractory CD19-Positive B-Cell Non-Hodgkin's Lymphoma (Amended Clinical Trial of Study TED6829)

Based on the clinical evidence of two late toxicities with late onset supported by PK data showing that steady state is reached after 3-4 weeks of treatment, the protocol described in EXAMPLE 1 was amended to evaluate an optimized schedule consisting of 4 weekly doses of 55 mg/m² followed by 4 additional doses administered once every 2 weeks (ongoing).

The STUDY OBJECTIVES and METHODS are identical to EXAMPLE 1, except that SAR3419 as single agent was administered IV under a schedule consisting of 4 weekly doses followed by 4 bi-weekly doses at the RD.

Furthermore the SAR3419 Drug Product was available as a concentrate solution for infusion at 125 mg/25 mL, i.e. 5 mg/ml with reference to the active entity supplied in a 30 mL clear glass vial.

The study of EXAMPLE 1 was extended to treat 25 patients with the optimized schedule.

Results

The results are summarized in the following tables 8-12.

TABLE 8

Baseline Demographics and Disease Characteristic

| | N |
|---|---|
| Treated | 25 |
| Evaluable for safety* | 25 |
| Evaluable for response* | 25 |
| Eligible for exploratory biomarkers sub-study (biopsy at study entry) | 13 |

TABLE 8-continued

Baseline Demographics and Disease Characteristic

| | N | |
|---|---|---|
| Age, median (range) | 70 (37-85) | |
| Male/Female | 12/13 | |
| ECOG PS (0/1/2) | 13/9/3 | |
| Histology | Initial diagnosis | Study entry |
| FL | 6 (24%) | 7 (28%) |
| DLBCL | 11 (44%) | 9 (38%) |
| MCL, MZL, other | 2, 1, 5 | 2, 2, 5 |
| Ann Arbor stage III/IV at study entry | 24 (96%) | |
| Median number of prior chemotherapy regimens (range) | 2 (1-8) | |
| Patients with prior rituximab-based therapy | 24 (96%) | |
| Patients refractory** to last regimen | 7 (28%) | |
| Last regimen containing rituximab | 3 | |
| Prior stem cell transplant autologous | 9 (38%) | |

*4 patients were mistakenly underdosed and received 40 mg/m²; 21 patients did actually receive the planned dose 55 mg/m²
**Refractory status = progressive under treatment or within 6 months after the end of treatment

TABLE 9

Clinical AE per patient (>10%), whatever the relationship to the study drug (N = 25)

| | All grades* | Grades 3-4** |
|---|---|---|
| Asthenia | 7 (28.0%) | 1 |
| Diarrhoea | 4 (16.0%) | 1 |
| Abdominal pain/upper | 4 (16.0%) | — |
| Nausea | 3 (12.0%) | — |
| Constipation | 3 (12.0%) | — |
| Bronchitis | 3 (12.0%) | — |
| Pyrexia | 3 (12.0%) | — |
| Myalgia | 3 (12.0%) | — |

*reversible grade 1 blurred vision and grade 1 paresthesia were reported in 1 patient each.
**Other gr 3-4 reported in the study (1 event each): uveitis, pyelonephritis, myocardial infarction, lymphoedema.

TABLE 10

Haematological toxicity (N = 25)

| Laboratory raw data | All grades | Gr 3 | Gr 4 |
|---|---|---|---|
| Leukopenia | 18 | 2 (1)* | 1 |
| Neutropenia | 12 | 3 (2)* | 3 (2)* |
| Anemia | 23 | 1 | — |
| Thrombocytopenia | 16 | 3 (2)* | 1 (0)* |

*2 patients received further anticancer therapy without being censored for haemotological reporting. 1 patient was deviant at study entry and included with grade 3 neutropenia/leukopenia.

TABLE 11

Anti-lymphoma activity of the qw/q2w schedule

| | |
|---|---|
| ORR (CR/PR) | 7/25 (28%) including 3 CRu* |
| ORR in DLBCL subtype | 3/9 (33%) |
| Tumor shrinkage | 64% |
| Response duration (weeks) | [8; 35+]** to be updated |

*1 CRu in a patient refractory to last regimen
**x patients still responding at the study cut-off date

TABLE 12

Mean (CV %) SAR3419 PK parameters after the first and the last SAR3419 dose

| | N | $t_{max}^{a}$ (day) | $C_{max}$ (µg/mL) | $AUC_{0-\tau}^{b}$ (µg · day/mL) | $C_{avg}$ (µg/mL) | $CL_{ss}$ (L/day) | $V_{ss}$ (L) | $t_{1/2}$ (day) |
|---|---|---|---|---|---|---|---|---|
| 1st SAR3419 administration | 20 | 0.06 [0.04-0.24] | 28.6 (19) | 107 (22) | 15.3 (22) | NA | NA | NA |
| Last SAR3419 administration (5th to 12th administration) | 9 | 0.06 [0.06-0.22] | 41.6 (26) | 260 (31) | 18.6 (31) | 0.438 (56) | 4.34 (28) | 7.99 (27) |

Cmax: maximum observed concentration; tmax: fist time to reach Cmax; AUC: area under concentration versus time curve; Cavg: average concentration over the dosing interval; CLss: clearance at steady state; Vss: volume of distribution at steady state; t½z: terminal elimination half-life.
$^{a}$ Median [min-max],
$^{b}$ $\tau$ corresponds to the dosing interval (7 days and 14 days after the 1st and the last administration, respectively);
NA: Not applicable Conclusions Median number of doses received was 8 as planned with a median relative dose intensity of 1.0 [0.8-1.0] at the RD.

The most frequent related TEAEs were asthenia in 5 (23.8%) patients (1 event being of grade 3) and gastrointestinal disorders in 7 (33%) patients. Reversible grade 1 blurred vision/corneal event occurred in 1 patient. Grade 3-4 haematological toxicities were minimal.

Tumor shrinkage was observed in 16 (64%) patients. Seven (28%) patients, achieved an objective response including 1 CR and 3 Complete Response (CRu). The response rate was essentially preserved in aggressive disease (3/9 DLBCL patients).

In conclusion the schedule consisting of 4 weekly doses followed by 4 bi-weekly doses shows an improved safety profile compared to prior tested schedules, with a clinical efficacy preserved essentially in aggressive lymphoma.

Overall Conclusions

SAR3419 MTD/RD was determined during this study as 55 mg/m² (maximum tolerated dose) whilst the maximum administered dose (MAD) was 70 mg/m².

The optimized administration schedule (55 mg/m$^2$ weekly/biweekly) showed an improved safety profile compared to prior tested schedules with apparent clinical control of the incidence and severity of ADC (corneal)/DM4 (neuro-, digestive and hematological) related-toxicities.

Anti lymphoma activity was observed in both schedules of administration, around 30% of patients at the 55 mg/m$^2$ MTD/RD, especially in patients with aggressive histology (DLBCL) at that dose in the weekly/biweekly recommended schedule of administration.

The invention claimed is:

1. A method of treating CD19+ B-cell malignancies symptom in a human patient in need thereof, said method comprising
   a) administering to said patient an initial dose of 55 mg/m² of an anti-CD19 maytansinoid immunoconjugate,
   b) administering to the patient at least 3 subsequent doses of 55 mg/m² of the anti-CD19 maytansinoid immunoconjugate separated in time from each other by about one week, and
   c) administering to the patient at least 3 further subsequent doses of 55 mg/m² of the anti-CD19 maytansinoid immunoconjugate separated in time from each other by about two weeks, wherein said anti-CD19 maytansinoid immunoconjugate comprises an antibody that specifically binds to a CD19 antigen comprising:
   a) a heavy chain CDR1 comprising SNWMH (SEQ ID NO.4); a heavy chain CDR2 comprising EIDPSDSYTN (SEQ ID NO.5); and a heavy chain CDR3 comprising GSNPYYYAMDY (SEQ ID NO.6); and
   b) a light chain CDR1 comprising SASSGVNYMH (SEQ ID NO:1); a light chain CDR2 comprising DTSKLAS (SEQ ID NO:2); and a light chain CDR3 comprising HQRGSYT (SEQ ID NO:3),
   wherein the maytansinoid is DM4; and wherein the antibody is conjugated to DM4 through N-succinimidyl 4-(2-pyridyldithio)butanoate (SPDB) linker.

2. The method according to claim 1, wherein the method minimizes eye related adverse events.

3. The method according to claim 2, wherein the occurrence of all grades of eye related adverse events is below 40%.

4. The method according to claim 2, wherein the occurrence of grade 3 or 4 eye related adverse events is below 13%.

5. The method according to claim 1, wherein said CD19+ B-cell malignancies symptom is a leukemia or a lymphoma.

6. The method according to claim 5, wherein said lymphoma is Non-Hodgkin's lymphoma (NHL).

7. The method according to claim 5, wherein said leukemia is Acute lymphoblastic leukemia (ALL).

8. The method according to claim 6, wherein said Non-Hodgkin's lymphoma is Diffuse Large B-cell lymphoma (DLBCL), a follicular lymphoma (FL), a Mantle cell lymphoma (MCL), a Marginal zone lymphoma (MZL), a Small lymphocytic lymphoma (SLL), or a Waldenström macroglobulinemia (WM).

9. The method according to claim 6, wherein said NHL is a relapsed or refractory NHL.

10. The method according to claim 6, wherein said NHL is a NHL expressing CD19.

11. The method according to claim 6, wherein said patient has already been treated for the NHL.

12. The method according to claim 6, wherein said patient has failed rituximab therapy.

13. The method according to claim 6, wherein said NHL is rituximab resistant.

14. The method according to claim 6, wherein said patient has received an autologous or allogeneic stem cell transplant.

15. The method according to claim 1, wherein the anti-CD19 maytansinoid immunoconjugate is administered intravenously.

16. The method according to claim 1, wherein the anti-CD19 maytansinoid immunoconjugate comprises an huB4 antibody conjugated to DM4 through an SPDB linker.

17. The method according to claim 1, wherein the anti-CD19 maytansinoid immunoconjugate has the following formula:

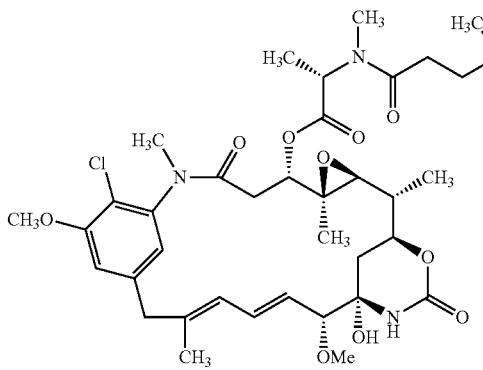

DM4

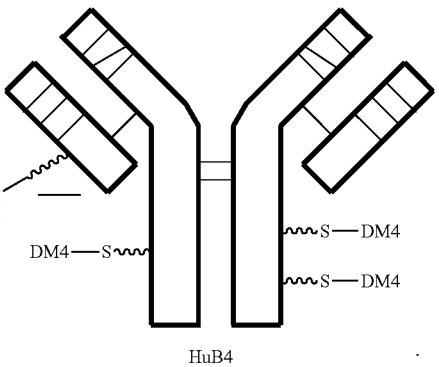

HuB4

18. The method according to claim 1, wherein the antibody comprises a light chain having the sequence of SEQ ID NO.7 and a heavy chain having the sequence of SEQ ID NO.8.

19. The method according to claim 16, wherein 3.5 molecules of DM4 are bound through the SPDB linker to each huB4 antibody molecule.

20. A method of treating CD19+ B-cell malignancies symptom in a human patient in need thereof, wherein the method comprises administering to the patient 4 doses of 55 mg/m² of an anti-CD19 maytansinoid immunoconjugate separated in time from each other by one week, and administering to the patient 4 subsequent doses of 55 mg/m² of the anti-CD19 maytansinoid immunoconjugate separated in time from each other by two weeks,
wherein said anti-CD19 maytansinoid immunoconjugate comprises an antibody that specifically binds to a CD19 antigen comprising:

a) a heavy chain CDR1 comprising SNWMH (SEQ ID NO.4); a heavy chain CDR2 comprising EIDPSDSYTN (SEQ ID NO.5); and a heavy chain CDR3 comprising GSNPYYYAMDY (SEQ ID NO.6); and
b) a light chain CDR1 comprising SASSGVNYMH (SEQ ID NO:1); a light chain CDR2 comprising DTSKLAS (SEQ ID NO:2); and a light chain CDR3 comprising HQRGSYT (SEQ ID NO:3),
wherein the maytansinoid is DM4; and wherein the antibody is conjugated to DM4 through N-succinimidyl 4-(2-pyridyldithio)butanoate (SPDB) linker.

21. The method of claim 20, wherein the antibody comprises a light chain having the sequence of SEQ ID NO.7 and a heavy chain having the sequence of SEQ ID NO.8.

22. The method of claim 20, wherein the antibody is HuB4 antibody.

* * * * *